United States Patent [19]

Sandel

[11] 4,318,473
[45] Mar. 9, 1982

[54] SURGICAL BLADE REMOVAL AND DISPOSAL DEVICE

[76] Inventor: Dan S. Sandel, 19524 Halsted St., Northridge, Calif. 91324

[21] Appl. No.: 216,426

[22] Filed: Dec. 15, 1980

[51] Int. Cl.³ .................... A61B 19/02; A61F 13/00
[52] U.S. Cl. ................................................. 206/370
[58] Field of Search ................ 206/370, 382, 63.5, 206/438, 359, 350, 354, 356; 232/43.1

[56] References Cited

U.S. PATENT DOCUMENTS

| | | | |
|---|---|---|---|
| 2,999,621 | 9/1961 | Kiser | 224/5 |
| 3,077,282 | 2/1963 | Eggers | 220/31 |
| 3,197,915 | 8/1965 | Staver | 43/57.5 |
| 3,518,593 | 6/1970 | Hall | 335/285 |
| 4,008,802 | 2/1977 | Freitag | 206/63.3 |
| 4,013,109 | 3/1977 | Sandel | 150/52 |
| 4,120,397 | 10/1978 | Neumann | 206/370 |
| 4,168,777 | 9/1979 | Gaskell et al. | 206/370 |
| 4,243,140 | 1/1981 | Thrun | 206/459 |

Primary Examiner—William T. Dixson, Jr.
Attorney, Agent, or Firm—Poms, Smith, Lande & Rose

[57] ABSTRACT

A case for disposing surgical blades includes an integral portion for removing the blade from a handle. The conventional blade has a key slot for receiving a inserted portion on the handle, which slides in the slot and passes through a wider portion of the slot permitting the blade to be removed from the inserted portion and handle. The blade has an edge at the rear of the slot for engaging a rear face of the inserted portion. Retaining members on the bottom wall of the case hold removed blades. The blade removing portion has a guide integral with the case for guiding the handle and its associated blade therethrough. The guide includes a slot deeper than the handle for receiving the handle and for permitting the handle to move downward. The guide also includes a shoulder positionable under the blade for supporting the rear of the blade. When the handle moves downward in the slot, the inserted portion pulls the central portion of the blade down causing it to bow on the shoulder and the forward portion of the case releasing the rear edge of the between the blade slot and the handle and permitting the slot of the blade to slide on the inserted portion. The guide also has a stop integral with the case rearward of the shoulder and above the top of the blade prior to bowing the blade for engaging the rear of the blade and for stopping rearward motion of the blade when it is bowed so that the inserted portion moves in the slot to a wider portion of the slot thereby disengaging the blade from the handle. An abutment forward of the guide and integral with the case positioned over the forward portion of the blade and a guard over the rear of the blade prevents the forward and rear portions of the blade from snapping off the case when the blade is disengaged from the inserted portion.

13 Claims, 6 Drawing Figures

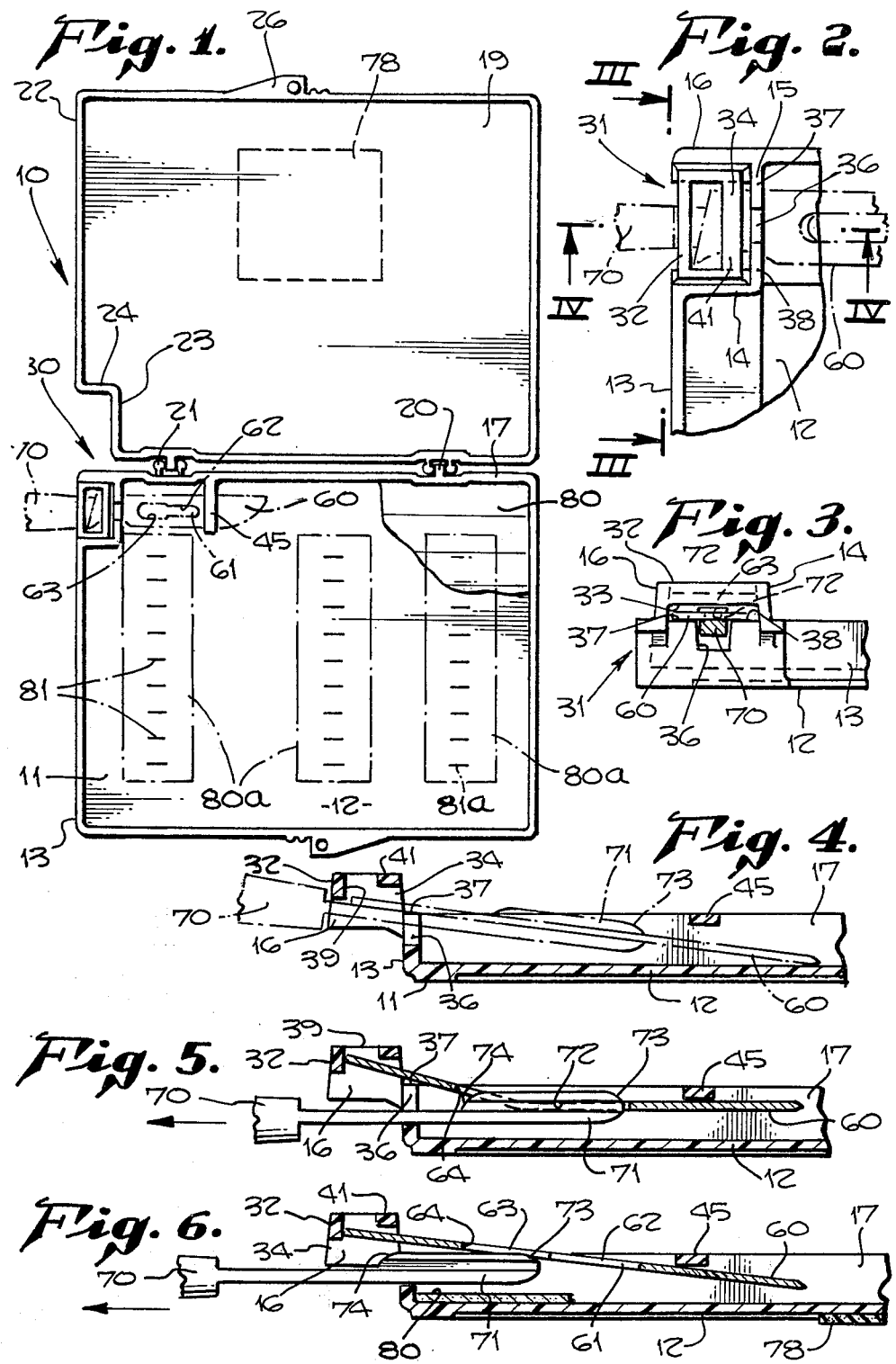

SURGICAL BLADE REMOVAL AND DISPOSAL DEVICE

BACKGROUND OF THE INVENTION

This invention relates to a device for removing used disposable surgical blades from handles and safely disposing contaminated blades. During the course of surgery, blades dull and must be replaced by a sharp, sterile ones.

A typical surgical knife handle is made by Bard-Parker. The blade for such a handle has a slot with a wider portion near the rear and a narrow portion forward. The handle has a narrow or inserted portion at the forward end that holds the blade. The narrow portion of the handle has a rounded front and rear with a groove on both sides. The front end is inserted into the wide part of the blade slot and the narrow portion of the slot slides in the grooves until the rear of the slot clears the rear of the handle narrow portion. The blade can flaten and the rear of the blade slot is held by the rear end of the narrow portion of the handle.

In the past when a blade was changed a member of the surgical staff would disengage the rear end of the slot of the blade from the rear end of the inserted portion of the handle using a surgical tool or his or her hand and begin sliding the blade slot along the inserted portion. This results in bending of the blade within its elastic limit so that when the inserted portion reaches the wide portion of the keyed slot, the blade has a tendency to snap upward. This is dangerous for it may cut someone, or it may be propelled away from the operating area where someone will have to retrieve it or where it may be lost temporarily. Members of the surgical staff are reluctant to use forceps or hemostates to remove blades, and if their hands slip among the blade, they may be cut.

The surgical staff must maintain strict accountability for all surgical instruments to insure that none remain in the patient after surgery. After removal of a blade, it is placed in a disposal unit so that an accounting can be made of the disposed blades, which when added to the number of unused blades must equal the number of new blades brought into the surgery. U.S. Pat. No. 4,013,109 (1977) discusses some of these requirements.

There have been prior attempts at constructing a device for removing blades safely, but they have been inoperable and could not be readily understood.

SUMMARY OF THE INVENTION

It is a primary object of the present invention to disclose and to provide an improvement in a surgical blade removal and disposal device allowing a blade to be removed from a handle safely in one motion and without touching the blade. A further object of the present invention is to disclose and to provide a device for safely removing a blade from a handle with parts that support the blade but permit the handle to be moved to bow the blade and release the detent portion of the blade and then prevent the blade from moving so that the handle can be withdrawn to where the knob is over the wider portion of the slot to the release the blade from the handle. A portion of the device prevents the blade from being propelled away from it upon release of the blade from the handle.

A further object of the present invention is to incorporate such a device into a disposal case such that a blade removed from a handle can be easily stored on a magnetic, adhesive or foam surface prior to and during disposal thereof so that strict accountability can be maintained. A further object of the present invention is to provide and to disclose such a device in a unitary, low cost, plastic case that sits flat. A further object is to disclose and provide a structure such that once the blade is removed from the handle, it can be easily located in the disposal case. Other objects will become readily apparent in the foregoing description of the invention.

BRIEF DESCRIPTION OF THE DRAWINGS

FIG. 1 is a plan view of the case having the surgical blade removal and disposal device of the present invention therein.

FIG. 2 is a plan view showing the surgical blade removal and disposal device of the present invention in detail.

FIG. 3 is an end view looking through plane III—III of FIG. 2 showing the blade removal and disposal device.

FIGS. 4, 5 and 6 are sectional views taken through plane IV—IV of FIG. 2. FIG. 4 shows the blade and handle (in phantom) inserted into the device, FIG. 5 shows the handle being detached from the blade, and FIG. 6 shows the blade completely detached from the handle.

DETAILED DESCRIPTION OF AN EXEMPLARY EMBODIMENT

A case 10 for disposing surgical blades including a portion 30 for removing the blade from a handle is shown in the exemplary embodiment in FIG. 1. The blade and handle used with the present invention are conventional, and although reference is made to blades, the present invention may be used for removing and disposing other surgical implements that are mounted on handles such as needles, saw blades and the like. A blade and its associated handle are shown in phantom in FIGS. 1-4. FIG. 1 shows the entire blade 60 mounted on handle 70. The blade has a keyed slot 61 with a narrow portion 62 and a wider portion 63 toward the rear of the slot. As best seen in FIG. 6, handle 70 has a inserted portion 71 with grooves 72 on either side. The inserted portion has rounded front and rear faces 73 and 74. The inserted portion is generally wider than the narrow portion 62 of the blade slot, but it fits through the wider portion 63 to allow removal of the blade and insertion of another blade onto the handle, and grooves 72 are deep enough to permit narrow portion 62 of the blade to engage the grooves and be held on the inserted portion. When the blade is in its normal position on the handle, the rear face 74 engages the rear edge 64 of blade slot 61, which prevents the blade from moving along its slot 61 on the grooves of inserted portion 71. Additionally, the rear edge 65 of the blade may abut a surface 75 (FIG. 4) of the handle to help prevent movement of the blade.

Manual removal of the blade creates problems because it is necessary to lift the rear end of the blade upward to disengage rear face 74 from rear edge 64 of blade slot 61 for permitting the blade to slide along grooves 72. If a person uses his or her hand to remove the blade, it is relatively easy for his or her fingers to slide to a sharp portion of the blade where the person may be injured. When the grooves of the inserted portion disengage the blade slot upon sliding, the spring energy of the blade is released and the blade may snap off the handle.

The case of the present invention is provided with a blade removing the disposal device. The device comprises a guide means at the rear of the device for guiding the handle and its associated blade therethrough. In the exemplory embodiment, the guide means 31 is located in the upper left-hand corner of bottom section 11 of case 10. In FIG. 3, the cross-section of the guide means 31 is shaped to conform generally to the shape of the handle and blade. The top of the blade is guided by the bottom of stop 32, whose bottom wall 33 extends just above the top of the blade during insertion of the blade into the guide means 31. Stop 32 is part of an upper guide member 34 integrally formed in the bottom portion 11 of case 10 as best shown in FIG. 2. Bottom portion 11 has a bottom wall 12 and an edge 13 around the perimeter. The edge bends around guide member 34 forming walls 14, 15 and 16 (FIG. 2). Stop 32 extends between walls 14 and 16. As seen in FIG. 3, walls 14 and 16 form the side of guide means 31.

The guide means also comprises a handle receiving portion. Referring to FIG. 3 in the exemplary embodiment, the handle receiving portion 36 is a cutout in wall 15 shaped to accommodate handle 70. The handle receiving portion 36 is deeper than the vertical thickness of the handle to allow the handle to move downward for reasons set forth below. The top of wall 15 are shoulders 37 and 38 that support the rear end of blade 60.

The device also includes a forward abutment positioned over the forward portion of the blade for preventing the forward portion of the blade from snapping up off the device when the blade is disengaged from the inserted portion of the handle. In the exemplary embodiment, the forward abutment 45 extends outward from the top portion 17 of edge wall 13 (FIGS. 2 and 4).

To operate the device, the blade and handle are inserted through the guide means so that the rear of the blade is over shoulders 37 and 38, and the more forward portion of the blade is under abutment 45 usually resting on the case. Handle 70 is then urged downward in handle receiving portion 36 which tends to bow blade 60 (FIG. 5). This disengages the rear face 74 of inserted portion 71 from the rear edge 64 of the blade slot 61 to allow the handle to slide relative to the blade. The blade tends to move with the handle in FIG. 5 from friction between the inserted portion 71 and the blade. Some of its movement may be restrained by friction from the shoulders and the abutment, but upon moving even a short distance, the rear edge of the blade 65 encounters front wall 39 of stop 32, which prevents any further movement of the blade to the left.

Continued movement of the handle to the left, however, slides grooves 72 along narrow portion 62 of keyed slot at 61 until narrow portion 62 is disengaged from the grooves (FIG. 6). When this occurs, the elasticity of the blade causes the center portion to snap upward away from the handle. A guard 41 is positioned above the blade (FIG. 6) to prevent the blade from springing off. Guard 41 is part of guide member 34 and extends between walls 14 and 16 (FIG. 2), and it is generally above and slightly to the rear of the front of shoulders 37 and 38.

Thereafter, the blade may be moved slightly to the right (FIG. 1) where it will be free to be slid down the retaining member 80, or it may be lifted and placed on the retaining member. In the exemplary embodiment, retaining member 80 is a magnetic sheet that fits into and is attached by adhesive to bottom wall 12. The retaining member may also be foam or adhesive strips 80A (in phantom). The retaining member may have indicia 81 or separations 81A for separating the blades for accounting purposes, and indicia may also be provided for that purpose.

The top of the case 19 is hinged at 20 and 21 to the bottom part of the case 11. The case is intended to lie flat on a flat surface when it is opened as in FIG. 1. Top 19 has a perimeter wall 22 extending around it. At walls 23 and 24, perimeter wall 22 juts inward to leave a space for accommodating guide member 34. Wall 23 rests on or slightly above shoulders 37 and 38, and wall 24 rests on or slightly above surface 40 (FIG. 3). The case is provided with opposing latches 25 and 26 to latch the case closed after it is used so that no blades fall out and strict accounting standards are maintained. The case may have one or more gripping members 78 for preventing sliding of the case.

Although this particular invention has been described in detail with particular reference to the exemplary embodiment, various modifications may be made to it by one skilled in the art and still come within the scope and spirit of the present invention, which is limited only as defined in the claims.

I claim:

1. A surgical blade removal and disposal device for removing a blade from a handle wherein the blade and handle has a locking portion near the rear of the blade preventing movement of the blade relative to the handle, and the blade has a key slot for receiving an inserted portion on the handle, the inserted portion being slidable in the slot and passing through a wider opening at a portion of the slot permitting the blade to be removed from the inserted portion and off the handle, the device comprising:
    (a) rigid guide means at the rear of the device for guiding the handle and its associated blade therethrough, the guide means comprising a handle receiving portion permitting the handle to move downward therein, and shoulder means under -the blade for supporting the rear of the blade, the forward portion of the blade contacting a forward surface of the device, whereby when the handle moves downward in the guide means, the inserted portion of the handle pulls the central portion of the blade downwardly causing it to bow on the shoulder and the forward surface, releasing the locking portion between the blade and the handle and permitting the slot of the blade to slide on the inserted portion;
    (b) the guide means further comprising stop means fixed in a position rearward of the shoulder and above the plane of the blade prior to bowing the blade for engaging the rear of the blade and for stopping rearward motion of the blade when it is bowed so that the inserted portion moves in the slot to the wider portion of the slot thereby disengaging the blade from the handle.

2. The device of claim 1 wherein the guide means further comprises a guard above the blade forward of the stop means and extending at least partially to the rear of the shoulder means when the blade is against the stop means to prevent the blade from springing off the device when the inserted portion moves to the wider portion of the slot disengaging the blade from the handle.

3. The device of claims 1 or 2 further comprising a forward abutment positioned over the forward portion of the blade for preventing the forward portion of the blade from springing off the device when the inserted portion moves to the wider portion of the slot disengaging the blade from the handle.

4. The device of claim 1 wherein the stop extends downward adjacent to but spaced from the blade when it is inserted in the guide means for guiding the blade and for engaging the rear edge of the blade when the blade is being removed from the handle.

5. A two part case for disposing surgical blades including a blade removing portion for removing the blade from a handle wherein the blade and handle has a locking portion near the rear of the blade and the blade has a key slot for receiving an inserted portion on the handle, the inserted portion being slidable in the slot and passing through a wider portion of the slot permitting the blade to be removed from the inserted portion and off the handle, the case having base with a bottom wall and side walls around the bottom wall with retaining members therein for retaining removed blades and a hinged protective cover which in the open position permits access to the base, wherein the improvement comprises:

the blade removing portion of the case being integral with the base, the portion for removing the blade comprising:

guide means integral with the case for guiding the handle and its associated blade therethrough, the guide means comprising a handle receiving portion permitting the handle to move downward therein and shoulder means positionable under the blade for supporting the rear of the blade; and the bottom wall being forward of the guide means positioned under the forward portion of the blade for supporting the forward portion of the blade whereby when the handle moves downward in the guide means, the inserted portion of the handle pulls the central portion of the blade down causing it to bow on the shoulder and the bottom wall releasing the locking portion detent between the blade and the handle and permitting the slot of the blade to slide on the inserted portion;

the guide means further comprising stop means integral with the base rearward of the shoulder and above the top of the blade prior to bowing the blade for engaging the rear of the blade and for stopping rearward motion of the blade when it is bowed so that the inserted portion moves in the slot to a wider portion of the slot thereby disengaging the blade from the handle the guide means further comprises a guard including a part extending from a sidewall above the blade when the blade is against the stop means to prevent the blade from springing off the case when the cover is open and when the inserted portion moves to the wider portion of the slot disengaging the blade from the handle.

6. The device of claim 5 further comprising a forward abutment integral with the base and positioned over the forward portion of the blade for preventing the forward portion of the blade from springing off the device when the inserted portion of the handle moves to the wider portion of the slot disengaging the blade from the handle.

7. The case of claim 5 wherein the retaining member is adjacent the blade removing portion for receiving a blade that has been removed from its associated handle.

8. The case of claim 5, wherein the blade removing portion is in a corner of the case.

9. The case of claim 5 or 8, further comprising a wall edge jutting inward from a sidewall about the blade removing portion, and the guide means being supported between the wall jutting inward and a portion of the remainder of the peripheral wall.

10. The case of claim 9 wherein the cover has a cut-out portion for receiving the top part of the guide means to permit the cover of the case to be closed.

11. The case of claim 9 further comprising locking means on the case for locking the cover of the case.

12. A method for removing a blade from a handle wherein the blade and handle has a locking portion near the rear of the blade and the blade has a key slot receiving an inserted portion on the handle, the inserted portion being slidable in the slot and passing through a wider opening at a portion of the slot permitting the blade to be removed from the inserted portion and off the handle, the method comprising:

(a) resting the rear of the blade on a shoulder and the forward portion of the blade on a forward surface;

(b) pulling the handle downward to bow the blade between the shoulder and the forward surface and to release the locking portion between the handle and the blade;

(c) urging the handle rearwardly and preventing rearward motion of the blade along with the handle until the inserted portion is over the wider portion of the key slot to release the blade from the handle.

13. The method of claim 11 further comprising blocking the vertical snap of the blade off of the handle to prevent the blade from being projected too far away from the handle.

* * * * *